Figure 1:
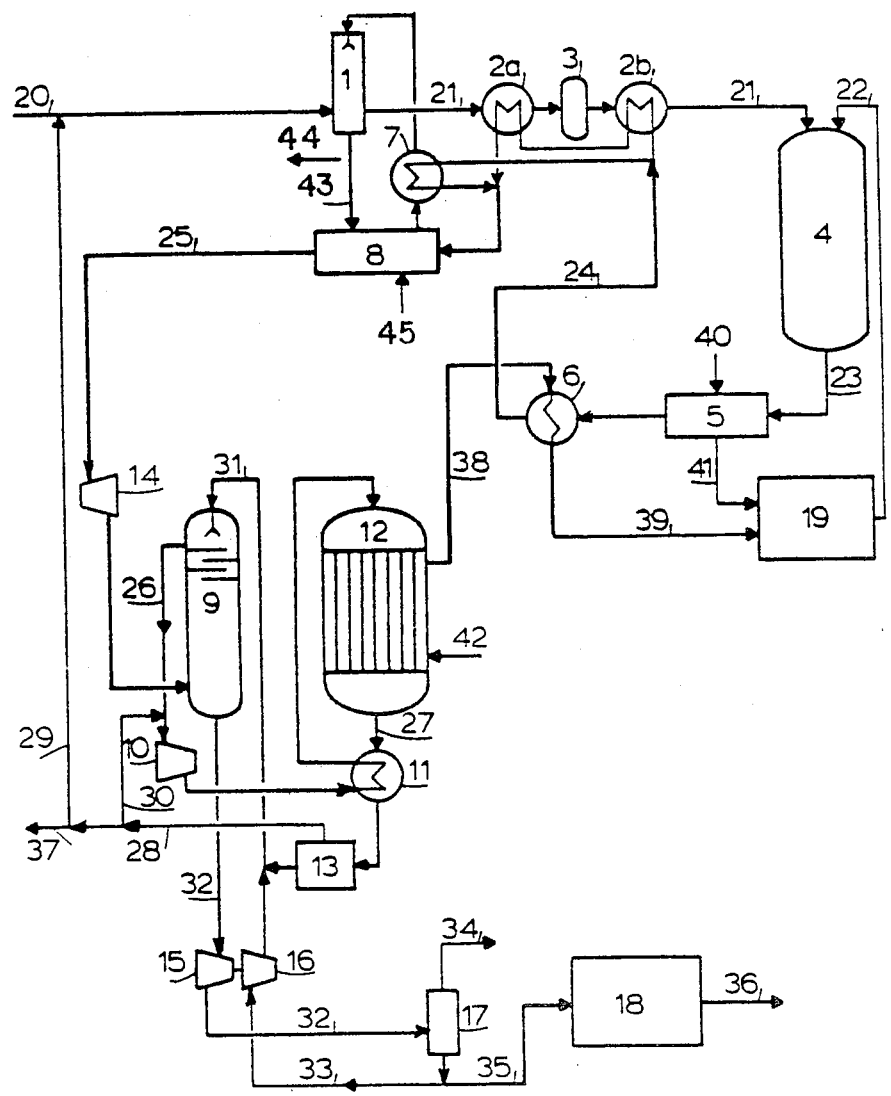

United States Patent [19]

de Lathouder

[11] Patent Number: 4,464,483
[45] Date of Patent: Aug. 7, 1984

[54] PROCESS FOR THE PREPARATION OF METHANOL

[75] Inventor: Hans C. de Lathouder, Geleen, Netherlands

[73] Assignee: Stamicarbon B.V., Geleen, Netherlands

[21] Appl. No.: 388,501

[22] Filed: Jun. 14, 1982

[30] Foreign Application Priority Data

Jun. 12, 1981 [NL] Netherlands .................. 8102840

[51] Int. Cl.$^3$ ............................................. C07C 27/06
[52] U.S. Cl. .................................... 518/703; 518/725
[58] Field of Search ........................................ 518/703

[56] References Cited

U.S. PATENT DOCUMENTS 3,920,717  11/1978  Marion .............................. 518/703

FOREIGN PATENT DOCUMENTS 2247441  6/1975  France ............................... 518/703
1309872  3/1973  United Kingdom ................ 518/703

Primary Examiner—Howard T. Mars
Attorney, Agent, or Firm—Cushman, Darby & Cushman

[57] ABSTRACT

The invention concerns the synthesis of methanol from lower hydrocarbons. The C1–3 hydrocarbons are subjected to partial oxidation over a catalyst in the presence of oxygen and steam, part of the carbon dioxide is removed from the effluent gas to adjust the ratio of hydrogen to carbon monoxide and carbon dioxide, and the resulting gas is converted to methanol in a steam generating reactor. The over all economy of the process is clearly better than that of conventional processes utilising a steam reformer.

3 Claims, 1 Drawing Figure

PROCESS FOR THE PREPARATION OF METHANOL

The invention relates to a synthesis of methanol, starting from lower hydrocarbons, by conversion of the hydrocarbons into a gas mixture containing carbon monoxide and hydrogen and catalytic conversion of the resulting mixture into methanol.

It is known to convert lower hydrocarbons, for instance natural gas, into a synthesis gas by passing the hydrocarbons with steam over an indirectly heated, nickel-containing catalyst at elevated temperature and pressure. Thus, a gas mixture is formed which contains more hydrogen than the stoichiometric amount formally required for methanol. A disadvantage of this process is a relatively high energy consumption. Furthermore, after the synthesis a residual amount of hydrogen is obtained, which can often be utilized only as fuel gas.

The object of the invention is a process for the preparation of methanol starting from lower hydrocarbons which has a low energy consumption and which does not require larger investments than for the known processes.

According to the invention the methanol is prepared by converting a hydrocarbon, or a mixture of hydrocarbons, containing 1–3 carbon atoms into a gas mixture containing carbon monoxide and hydrogen, and converting this at elevated temperature and pressure in the presence of a suitable catalyst into methanol, the improvement residing in converting the hydrocarbon with oxygen and water by partial oxidation in the presence of a suitable catalyst at an outlet temperature of between 800° and 1200° C. and a pressure of between 20 and 100 bar, into a gas mixture substantially consisting of carbon monoxide, carbon dioxide and hydrogen, removing from this gas mixture such an amount of carbon dioxide by absorption in a suitable medium, that the $H_2/2CO+3CO_2$ molar ratio is between 0.95 and 1.05, and supplying this gas mixture to a reactor, in which at a temperature of between 240° and 320° C. and a pressure of between 40 and 100 bar in the presence of a suitable catalyst, it is converted into methanol, which methanol, after cooling and expansion to approximately atmospheric pressure, is separated off and sent to a purification section, the energy released in the partial oxidation and in the methanol synthesis being applied for the generation of steam in an amount sufficient to meet the energy requirements of an oxygen separation plant supplying the oxygen required for the partial oxidation.

Essential steps in the process therefore are the partial oxidation yielding a gas mixture containing CO, $CO_2$, $H_2$ and $H_2O$, the removal of such an amount of $CO_2$ from the gas mixture that the desired ratio is obtained, and the carrying out of the methanol synthesis in a reactor in which the heat of reaction is converted into medium-pressure or high-pressure steam. Advantages of the process according to the invention are a very low energy consumption per ton of methanol produced, the fact that only carbon dioxide is obtained as by-product, the redundancy of a steam reformer and the absence of a separate water-gas shift reactor.

As feed for the process methane, ethane or propane or a mixture of these is used. If necessary, the hydrocarbons can be desulphurized before being fed to the process or at any stage of the process prior to the methanol synthesis. The pressure of the gas mixture preferably is chosen to be between 20 and 100 bar, more particularly between 30 and 60 bar.

The partial oxidation of hydrocarbons is known in itself. It comprises passing the gaseous hydrocarbon with oxygen over a suitable catalyst, for instance a nickel-containing catalyst, at a pressure of between 20 and 100 bar and a temperature of between 800° and 1200° C. This partial oxidation is used virtually exclusively for the conversion into synthesis gas of higher hydrocarbons such as fuel oil or cracked petrol. Up to now a steam reformer has been considered more suitable for processing of lower hydrocarbons. The applicant has now found that the application of partial oxidation in a methanol synthesis starting from hydrocarbons containing 1–3 carbon atoms does offer special advantages after all, and that notably the amount of methanol produced per kmol hydrocarbon may be 10 to 20% larger than in a conventional process using a steam reformer. It is also possible to prepare a suitable synthesis gas mixture by operating a steam reformer and a reactor for partial oxidation in parallel and mixing the two resulting gas streams. Further, a steam reformer and a secondary reformer arranged in series can be used. Such processes however are less efficient than the process according to the invention, since they still use the energetically inefficient steam reformer. They also would be more complicated and would require higher investment costs.

By adding water to the hydrocarbon mixture, an equilibrium reaction immediately occurs in the reactor, carbon dioxide and hydrogen being formed from carbon monoxide and water, so that the evolving gas mixture becomes relatively richer in hydrogen. A separate water-gas shift reactor therefore is superfluous. The partial oxidation is preferably carried out at a pressure of between 30 and 60 bar and a temperature of between 900° and 110° C. The temperature indicated is the outlet temperature, i.e. the temperature of the gas leaving the reactor. The catalysts now commercially available are generally designed for use pressure of at most about 35 bar. Higher pressures can be used however in the process according to the invention if a shortened catalyst life is accepted or improved catalysts are used.

The amount of water supplied to the reactor may vary between fairly wide limits. A molar ratio between water and carbon (introduced as hydrocarbon) will generally be between 1.0 and 2.5 although somewhat higher or lower ratio's, e.g. between 0.5 and 5 could be used. The most preferred ratio is between 1.2 and 2.0. The water can be supplied by evaporating, with the aid of a saturator, hot water in the hydrocarbon feed flow and, if necessary, in the oxygen feed flow. The feed of the partial oxidation reactor is preheated, preferably to a temperature of between 500° and 700° C. The hot gas mixture, consisting of a mixture of substantially CO, $CO_2$, $H_2$ and $H_2O$ leaving the reactor, is cooled. The heat is utilized for generating/superheating steam, for heating the feed gas and for evaporating water in the saturator(s). A significant part of the water vapor condenses at this stage. By further cooling to, for instance, a temperature of between 20° C and 40° C. the remaining water is condensed and separated.

The composition of the gas mixture now is to be chosen so that the ratio between hydrogen on the one hand and carbon monoxide and carbon dioxide on the other reaches the value desired for the methanol synthesis, which implies that part of the carbon oxides is to be removed. It has been suggested to partially scrub out the carbon monoxide. This, however, requires a scrubbing operation with a special scrubbing liquid at a low temperature. In the process according to the invention the desired ratio is obtained by scrubbing out part of the carbon dioxide. To achieve this, known processes can be applied in which the gas stream is scrubbed with a special scrubbing medium such as N-methylpyrrolidone, triethanolamine, a potassium carbonate solution or methanol cooled to a low temperature. These processes often are also effective at a low partial pressure of the carbon dioxide. The entire gas stream may be subjected to a scrubbing operation, in which case not all carbon dioxide need be removed, or all or practically all carbon dioxide may be removed from part of the gas stream. In both cases, however, it is disadvantageous that a separate regeneration of the scrubbing liquid, with separation of carbon dioxide, is required. According to a preferred embodiment of the process according to the invention, the gas stream is scrubbed at a temperature of between 15° C. and 40° C. using crude methanol from the synthesis reactor that has not yet been expanded, the pressure used being approximately equal to the methanol synthesis pressure, i.e. by preference at a pressure of between 70 and 90 bar. In this way the $CO_2$ content of the gas stream can be reduced only to a limited extent, and a relatively high partial pressure of the carbon dioxide in the gas mixture is required. If the conditions are properly chosen, however, it still is well possible to achieve the desired ratio between hydrogen on the one hand and carbon monoxide plus carbon dioxide on the other. This embodiment has the advantage that no separate regeneration step is required and that it is not necessary to apply extra cooling of the gas stream before the scrubbing operation. The $CO_2$-loaded crude methanol can be expanded to about atmospheric pressure, so that the carbon dioxide is again released. The crude methanol can subsequently be transported to the purification section of the plant. Optionally, part of it may also be recycled to the scrubbing section after compression. The required compression energy is obtained practically entirely by expansion of the carbon dioxide-loaded methanol.

In the gas supplied to the methanol synthesis reactor the $H_2/2\ CO+3CO_2$ molar ratio is between 0.95 and 1.05 and preferably between 1.00 and 1.04. The gas mixture may contain 62 and 74% by volume of hydrogen, 19 to 24% by volume of CO and 3 to 10% by volume of $CO_2$, besides possibly minor amounts of non-converted hydrocarbon and/or inert gas. A suitable gas contains for instance 70% by volume of hydrogen, 22% by volume of carbon monoxide and 8% by volume of carbon dioxide. The synthesis gas mixture is, if necessary, brought at synthesis pressure and preheated, either prior to the scrubbing operation or later.

The methanol synthesis takes place in a reactor operating at a temperature of between 240° C. and 320° C. and a pressure of between 40 and 100 bar in the presence of a suitable catalyst. By preference, the pressure is between 70 and 90 bar and the temperature between 250° C. and 270° C. The reactor is to be designed for discharging of the heat of reaction with simultaneous steam generation. Suitable reactors and reaction conditions are known and described in literature, i.e. as 'steam raising synthesis'. The known catalysts, e.g. on the basis of copper oxide, zinc oxide or chromium oxide, may be used.

The gas leaving the synthesis reactor is cooled to a temperature of between 15° C. and 40° C., upon which the methanol is condensed and separated. Part of the residual gases can be vented and the remaining part is returned to the process, mainly to the synthesis section. Preferably, a part of the gas is also recycled to the reactor wherein the partial oxidation is carried out. The amount of recycled gas is such that the reactor feed contains between 0.05 and 0.5 moles of hydrogen for every mole of hydrocarbon, and preferably between 0.1 and 0.4 moles of hydrogen. Such a recycle makes it possible to carry out the partial oxidation at a relatively low temperature and a relatively low ratio of water to carbon, two factors which increase the economy of the process.

The process according to the invention will be described on the basis of a FIGURE. Via line 20 the gaseous hydrocarbon is supplied to a saturator 1, in which water vapour is added to the gas. Through line 21 and via heat exchangers 2a and 2b, and optionally desulphurization plant 3, the water-containing gas is sent to reactor 4. The desulphurization of the gas may also be carried out in another place, for instance prior to the saturator or in combination with the removal of carbon dioxide. Via line 22 practically pure oxygen is supplied from oxygen separation plant 19 to the reactor. In the reactor the gas mixture is converted over a catalyst containing nickel oxide into a gas substantially containing carbon monoxide, carbon dioxide and hydrogen, which is transported via line 23 to steam generator 5, in which the boiler feed water supplied via line 40 is converted into high-pressure steam, and from there it is passed to cooling and condensation plant 8 through line 24 via heat exchanger 6, heat exchangers 2b, 2a and 7. The heat of the gas mixture is thus used for the generation of high-pressure steam and for heating the feed and the water supplied to the saturator. In plant 8 the remaining heat is utilized for preheating of the saturator feed and of boiler feed water and the gas is cooled further and the condensed water separated off. Via line 45 water is supplied to plant 8 which, together with condensed and separated water after heating is supplied to the saturator 1 via heat exchanger 7. Water from the saturator is in part recycled to plant 8 via line 43 and in part drained via line 44. Through line 25 the gas is transported to compressor 14, where it is brought to the synthesis pressure, and hence to scrubber 9, in which it is scrubbed with crude methanol, supplied via line 31. The scrubbed gas, which now has the composition desired for the methanol synthesis, is sent via line 26 to compressor 10, which ensures the transport of feed gas and recycle gas, and from there passed to synthesis reactor 12 via feed preheater, 11. Via line 27 and heat exchanger 11 the methanol-containing gas mixture formed is passed to plant 13, where it is cooled and the methanol formed and the non-converted gaseous components are separated. Via line 28 the gases are discharged. Part is recycled to the synthesis reactor via line 30, part is vented via line 37, and part is mixed with the hydrocarbon via line 29. The crude methanol is sent to gas scrubber 9 via line 31. The carbon-dioxide loaded methanol formed here is discharged via line 32 to turbine 15, in which the methanol is expanded, following which the carbon dioxide is separated in separator 17 and discharged via line 34. Part of the methanol is transported via line 35 to purification section 18, from which it is discharged as pure methanol via line 36. Another part is returned to the scrubber through lines 33 and 31 via compressor 16. In the synthesis reactor the boiler feed water supplied via line 42 is coverted into steam, which is supplied to oxygen separation plant 19 via line 38, heat exchanger 6 and line 39. The tangible heat of the gas mixture leaving the partial oxidation reactor 4 is utilized for converting the boiler feed water supplied to steam generator 5 via line 40 into high-pressure steam which is also supplied to the oxygen separation plant via line 41.

The process will be elucidated on the basis of an example without being retricted to the embodiment described in it.

EXAMPLE

A mixture consisting of methane (0.94 kmol) and nitrogen (0.01 kmol) is mixed with a recycle stream containing 0.06 kmol of methane, 0.33 kmol of hydrogen, 0.04 kmol of CO, 0.08 kmol of $CO_2$ and 0.2 kmol of nitrogen at a pressure of 35 bar, and after preheating to 540° C. it is supplied to partial oxydation reactor 4. Saturator 1 is fed with water that has been preheated at 200° C. Part of the water (0.28 kmol) comes from the methanol purification unit. Of the water from the saturator, 0.14 kmol is drained. To the saturator further some externally generated heat is supplied. To reactor 4 furthermore 0.56 kmol oxygen and 0.01 kmol nitrogen are supplied. After the conversion over the nickel containing catalyst, a gas mixture consisting of 0.71 kmol CO, 0.34 kmol $CO_2$, 2.26 kmol $H_2$, 1.54 kmol $H_2O$ and 0.21 kmol $N_2$ and 0.07 kmol $CH_4$ leaves the reactor at a temperature of 954° C. In the steam generator 23.6 kg steam, with a temperature of 500° C. and a pressure of 120 bar, is generated. The gas mixture is cooled by heat exchange with the feed and the water to be supplied to the saturator and is further cooled to 30° C. in unit 8. The condensed water is separated off and the residual gas mixture is compressed to 80 bar and scrubbed with 2 kmol methanol at 30° C. in scrubber 9. The scrubber gas, containing 0.71 kmol CO, 0.27 kmol $CO_2$, 2.26 kmol $H_2$, 0.21 kmol $N_2$, 0.07 kmol $CH_4$ and 0.01 kmol methanol, is compressed to 85 bar and preheated to 240° C. before being supplied to the synthesis reactor. The heat of reaction is utilized for the generation of 30.4 kg steam with a pressure of 36 bar and a temperature of 250° C., which is heated further to 480° C. in heat exchanger 6. The gas from the synthesis reactor is cooled to 30° C., upon which the methanol is separated off. Of the remaining gas, a part is vented and the remainder, having the composition described above, is recycled. The crude methanol is sent to scrubber 9. The methanol leaving the scrubber is expanded to about 1 bar over turbine 15 and the $CO_2$ liberated (0.06 kmol) is vented. Of the methanol a part corresponding to the amount from the synthesis (0.85 kmol methanol and 0.19 kmol water) is led to the purification section, while the remaining part is recycled to the scrubber after having been compressed to 80 bar.

I claim:

1. In a process for the preparation of methanol by converting a hydrocarbon feed containing a hydrocarbon having from 1-3 carbon atoms or a mixture thereof into a gas mixture containing carbon monoxide and hydrogen, and converting this gas mixture at elevated temperature and pressure in the presence of a suitable catalyst into methanol, the improvement comprising the steps of:

introducing said hydrocarbon feed into a partial oxidation zone, together with oxygen, between 1.0 and 2.5 mols of water per mol of carbon, and recycle non-converted gaseous components hereinafter referenced in an amount such that between 0.05 and 0.50 mol of hydrogen is introduced into said partial oxidation zone for every mole of hydrocarbon, wherein said hydrocarbon feed is partially oxidized at a pressure of between 30 and 60 bar and a partial oxidation zone outlet temperature of between 900° and 1100° C., in the presence of a suitable catalyst to form a first gas mixture substantially consisting of carbon monoxide, carbon dioxide, hydrogen, and water;

introducing said first gas mixture into a scrubbing zone wherein a portion of the carbon dioxide contained in said first gas mixture is removed therefrom by adsorption into methanol at a pressure of between 40 and 100 bar and at a temperature of between 15° and 40° C. to form a carbon dioxide-loaded methanol stream and a second gas mixture having an $H_2/2 CO + 3 CO_2$ molar ratio of between 0.95 and 1.05;

feeding said second gas mixture into a synthesis reaction zone wherein it is converted in the presence of a suitable catalyst and at a temperature of between 240° and 320° C. and a pressure of between 40 and 100 bar to form a third gas mixture containing methanol;

cooling said third gas mixture and separating a crude methanol stream from remaining non-converted gaseous components including hydrogen;

recycling at least a portion of said remaining non-converted gaseous components to said partial oxidation zone;

introducing at least a portion of said crude methanol stream into said scrubbing zone wherein it is utilized to absorb carbon dioxide from said first gas mixture to form said carbon dioxide-loaded methanol stream; and expanding said carbon dioxide-loaded methanol stream from said scrubbing zone to approximately atmospheric pressure whereupon carbon dioxide is removed therefrom and at least a portion of the resulting methanol stream is further purified to form product methanol, wherein the energy released in said partial oxidation zone and said synthesis reaction zone is utilized for the generation of stream in an amount at least sufficient to provide the energy requirements of an oxygen separation plant of sufficient capacity to provide said oxygen introduced into said partial oxidation zone.

2. Process according to claim 1, characterized in that a molar ratio between water and carbon in the feed of between 1.2:1 and 2.0:1 is applied.

3. Process according to claim 1, characterized in that a gas mixture is supplied to the reactor which contains between 19 and 24% by volume of CO, between 3 and 10% by volume of $CO_2$ and between 62 and 74% by volume of $H_2$, at an $H_2/2 CO + 3 CO_2$ molar ratio between 1.00 and 1.04.

* * * * *